United States Patent [19]

Orofino et al.

[11] Patent Number: 5,520,907
[45] Date of Patent: May 28, 1996

[54] CLEAR ANTIPERSPIRANT STICKS

[75] Inventors: Steven A. Orofino, Stratford; Matthew F. Kuznitz, Branford, both of Conn.

[73] Assignee: Chesebrough-Pond's USA Co., Division of Conopco, Inc., Greenwich, Conn.

[21] Appl. No.: 215,989

[22] Filed: Mar. 22, 1994

[51] Int. Cl.$^6$ .................................................. A61K 7/32
[52] U.S. Cl. ........................... 424/65; 424/66; 424/67; 424/68
[58] Field of Search ................................ 424/65, 66, 67, 424/68

[56]     References Cited

U.S. PATENT DOCUMENTS

| | | | |
|---|---|---|---|
| 4,154,816 | 5/1979 | Roehl et al. | 424/68 |
| 4,346,079 | 8/1982 | Roehl | 424/65 |
| 4,518,582 | 5/1985 | Schamper et al. | 424/66 |
| 4,719,102 | 1/1988 | Randhawa et al. | 424/66 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,948,578 | 8/1990 | Burger | 424/68 |
| 5,306,486 | 4/1994 | McCook | 424/59 |

FOREIGN PATENT DOCUMENTS 0512770  11/1992  European Pat. Off..

OTHER PUBLICATIONS

Jones, T. Minister, P (1993) Soap Perfumery & Cosmetics. 66 (7), 28.

*Primary Examiner*—Ceila Chang
*Assistant Examiner*—Evelyn Huang
*Attorney, Agent, or Firm*—Milton L. Honig

[57]     ABSTRACT

Antiperspirant compositions in gel form are provided which include an antiperspirant-active salt, a $C_2$–$C_6$ polyhydric alcohol, dibenzyl monosorbitol acetal, and a propoxylated $C_6$–$C_{20}$ alcohol carboxylate. The carboxylate serves both as an emollient and as a clarifier to obtain a clear gel stick.

6 Claims, No Drawings

CLEAR ANTIPERSPIRANT STICKS

BACKGROUND OF THE INVENTION

1. Field of the Invention

The invention relates to antiperspirant compositions in the form of gelled sticks.

2. The Related Art

Cosmetic sticks which exhibit a clear appearance can be prepared using sodium stearate as a gelling agent or structurant. Unfortunately, these clear sticks cannot be formulated with antiperspirant-active salts because the alkaline gelling agents will react with the acidic salts. This incompatibility has been surmounted through use of neutral structurants, for instance, use of low melting point waxy materials such as stearyl alcohol. Stability is good but the resultant sticks are opaque.

For many years, the art has investigated a unique gelling agent known as dibenzyl monosorbitol acetal (DBMSA) for use in translucent or transparent sticks. No derivative of sorbitol or any other gelling agent has yet been found which equals its structurant properties. However, it is also known that acetals are stable only in alkaline or neutral media, but not in acidic media. Under an acidic environment even in the presence of small amounts of water, the acetal hydrolyzes or will react with alcohol, e.g. ethanol, to form a different acetal.

Thus, antiperspirant sticks containing acidic antiperspirant-active salts in the presence of DBMSA in reactive alcoholic solvents have not been satisfactory because, in time, especially at elevated temperatures, they deteriorate and liquefy. There is a need, therefore, to find a way to stabilize these sticks against such deterioration.

Antiperspirant sticks containing dibenzyl monosorbitol acetal and antiperspirant-active salts are disclosed in U.S. Pat. No. 4,154,816 (Roehl et al.). These sticks contain, in addition to the antiperspirant-active salt and DBMSA, a lower monohydric alcohol, a di- or trihydric alcohol, a propylene-/ethylene-glycol polycondensate, and optionally an alkylolamide. A problem with these products is their stickiness on application. U.S. Pat. No. 4,346,079 (Roehl) reports elimination or significant reduction of the stickiness problem through replacement of at least part of the polycondensate with an oleaginous compound.

U.S. Pat. No. 4,518,582 (Schamper et al.) found the Roehl antiperspirant sticks, even with the improved stickiness control, were not stable on extended exposure at elevated temperatures. The problem was addressed through use of a gel stabilizer such as magnesium sulfate, zinc acetate and hexamethylenetetramine. Another remedy for stickiness is disclosed in U.S. Pat. No. 4,720,381 (Schamper et al.) wherein non-reactive solvents were used to replace reactive ones. Less reactive alcohols were identified as isopropanol, isobutanol, dipropylene glycol and other higher molecular weight alcohols. A still further approach was described in U.S. Pat. No. 4,725,430 (Schamper et al.) wherein N-(2-hydroxyethyl)acetamide was utilized as a stabilizing agent in the gel.

Another refinement of the DBMSA system is reported in U.S. Pat. No. 4,781,917 (Luebbe et al.) which utilizes a coupling agent and buffering adjustment agent to improve the stick. The coupling agent may be a polypropylene glycol (PPG) ether of a $C_4$–$C_{22}$ fatty alcohol. Suitable buffering adjustment agents were stated to be coconut monoethanolamide, sodium aluminum chlorohydroxylactate, sodium hydroxide, stearamide monoethanolamide, acetamide MEA, zinc acetate, zinc oxide, zinc stearate, zinc carbonate and similar materials.

U.S. Pat. No. 4,743,444 (McCall) describes improvements in gel rheology and transparency, while maintaining hardness and physical integrity. These benefits were obtained by incorporation of a $C_{14}$–$C_{16}$ fatty alcohol.

U.S. Pat. No. 4,719,102 (Randhawa et al.) in conjunction with a DBMSA gel stick describes novel solvents for use therein to allow processing at lower temperatures. The novel solvent is a compound having not greater than about five carbon atoms that includes, for instance, morpholine, pyridine, acetic acid, ethylene carbonate, propylene carbonate, etc.

EP 0 512 770 A1 (Benfatto et al.) describes DBMSA compositions wherein water and lower monohydric alcohols have been replaced with dihydroxy aliphatic alcohols containing 3 to 6 carbon atoms as solvents.

Westwood Chemical Corporation in its data sheets has suggested that a DBMSA gel stick could be stabilized with zinc glycinate. At higher temperatures this technology is insufficiently effective to prevent cloudiness arising in the gel stick. Clarity is especially adversely effected when the compositions contain emollients necessary to improve product aesthetics and avoid the tacky feel associated with this type of formulation.

Accordingly, it is an object of the present invention to provide an antiperspirant stick gelled with DBMSA which does not deteriorate or become sticky, even at higher temperatures.

Another object of the present invention is to provide an antiperspirant stick gelled with DBMSA that not only is stable but has good clarity, i.e. at least translucent if not transparent.

Still another object of the present invention is to provide an antiperspirant stick gelled with DBMSA that includes emollients yet minimizes the tacky feel commonly associated with these types of formulations.

These and other objects of the present invention will become more readily apparent from consideration of the following summary, examples and detailed description.

SUMMARY OF THE INVENTION

An antiperspirant composition is provided which includes:

(i) from about 1 to about 50% by weight of an antiperspirant-active salt;

(ii) from about 5 to about 60% of a $C_2$–$C_{12}$ polyhydric alcohol;

(iii) from about 0.5 to about 10% of dibenzyl monosorbitol acetal; and (iv) from about 0.1 to about 10% of a propoxylated $C_6$–$C_{20}$ alcohol carboxylate.

Use of the propoxylated alcohol carboxylate provides an emollient which not only improves aesthetics and reduces the tacky feel commonly associated with DBMSA formulations but also is highly compatible thereby maintaining product clarity.

DETAILED DESCRIPTION OF THE INVENTION

Now it has been discovered that the tackiness and aesthetics of a DBMSA gelled antiperspirant stick can be improved through use of a propoxylated $C_6$–$C_{20}$ carboxylate as an additive. Thus, the essential components of gelled sticks according to the present invention are an antiperspirant-active salt, at least one polyhydric alcohol as solvent, DBMSA as gellant and the propoxylated $C_6$–$C_{20}$ carboxylate.

Accordingly, the first essential element of compositions according to the present invention is an atiperspirant-active salt. Actives within this category include: polyhydroxy complexes of basic aluminum salts (e.g. aluminum chlorohydrol-propylene glycol complex), polyhydroxy derivatives of zinc and zirconium complexes of basic aluminum halides, zirconal hydroxychloride salts (e.g. zirconium/aluminum glycine complexes known as "ZAG"), aluminum chlorhydroxide, aluminum chloride, aluminum sesquichlorhydroxide and activated aluminum chlorhydroxide.

Particularly preferred is aluminum/zirconium pentachlorhydrex-GLY complex, fortified with zinc glycinate, and available from Westwood Chemical Corporation as Westchlor® A2Z8106 (30% propylene glycol solution).

Levels of the antiperspirant-active salt may range from about 1 to about 50%, preferably from about 10 to about 40%, optimally between about 15 and about 30% by weight.

A second essential element of compositions according to the present invention is that of a polyhydric alcohol functioning as a solvent for the composition. Polyhydric alcohols may be selected from the group consisting of 1,2-propylene glycol; 1,3-propylene glycol; 1,3-butylene glycol; glycerin; 2-methyl-2,4-pentane-diol; 2-ethyl-1,3-hexane-diol; 1,4-dihydroxypentane; 1,4-butylene glycol; dipropylene glycol; dibutylene glycol and mixtures thereof. Levels of polyhydric alcohol may range from about 5 to about 60%, preferably from about 10 to about 50%, optimally between about 25 and 40% by weight.

Dibenzyl monosorbitol acetal to be utilized in compositions of the present invention is commercially available as Millithix 925 from Milliken Chemical, Division of Milliken & Company and as Gell A-D from the New Japan Chemical Company, Ltd., Osaka, Japan. Levels of DBMSA should range from about 0.5 to about 10%, preferably from about 1.5 to about 5%, optimally between about 1.8 and 3% by weight.

The improvement element of compositions according to the present invention is that of a propoxylated $C_6$–$C_{20}$ alcohol carboxylate. The preferred carboxylate has the formula:

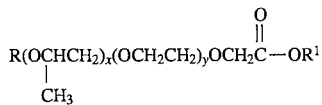

$$R(OCHCH_2)_x(OCH_2CH_2)_yOCH_2\overset{O}{\overset{\|}{C}}-OR^1$$
$$|$$
$$CH_3$$

wherein R is a $C_6$–$C_{20}$ radical selected from the group consisting of alkyl, alkenyl, cycloalkyl and phenyl; $R^1$ is a $C_1$–$C_8$ radical selected from the group consisting of alkyl, alkenyl, cycloalkyl and phenyl; x is an integer from 1 to 20, preferably from 1 to 5, optimally 2; and y is an integer from 0 to 20, preferably from 1 to 8, optimally about 6. The preferred R group is a $C_6$–$C_{12}$, optimally a $C_8$–$C_{10}$ alkyl group. $R^1$ is preferably a $C_1$–$C_4$ alkyl, optimally an isopropyl group. Most suitable for purposes of this invention is a material whose CTFA name is Isopropyl PPG-2-Isodeceth-7 Carboxylate, available as Velsan D8P-3 from the Sandoz Chemical Company. Levels of the carboxylate component will range from about 0.5 to about 10%, preferably from about 0.8 to about 5%, optimally between about 1 and 2% by weight.

A variety of buffering/pH adjustment agents may also be incorporated into compositions according to the present invention. Illustrative of this category are coconut monoethanolamide, sodium hydroxide, sodium carbonate, sodium bicarbonate, potassium hydroxide, potassium carbonate, potassium bicarbonate, magnesium oxide, magnesium hydroxide, magnesium carbonate, stearamide monoethanolamide, acetamide MEA, calcium carbonate, calcium oxide, aluminum oxide, calcium acetate, zinc glycinate, zinc oxide, zinc acetate and mixtures thereof. Most preferred is zinc glycinate. Levels of these agents may range from about 0.1 to about 10%, preferably from about 0.4 to about 3%, optimally from about 0.5 to about 1.5% by weight.

Emollients and coupling agents may also be included in compositions according to the present invention. Often, materials will function both as emollient and coupling agent. Illustrative of these materials are $C_6$–$C_{22}$ fatty alcohols, ethoxylated derivatives of $C_6$–$C_{22}$ fatty alcohols, propoxylated derivatives of $C_6$–$C_{22}$ fatty alcohols, and mixtures thereof. Specific examples of these are: PPG-5-ceteth-20; PPG-4 myristyl ether; PPG-4 lauryl ether; PPG-10 cetyl ether; PPG-3 myristyl ether; Glycereth 7; PPG-10 butane diol and mixtures thereof. Most preferred is PPG-10 butane diol (available as Macol 57) and Glycereth 7 (available as Liponic EG-7). Levels of these materials may range from about 0.1 to about 20%, preferably from about 0.5 to about 10%, optimally from about 0.8 to about 3% by weight.

Co-gellants may also be included in compositions according to the present invention. Particularly preferred are the ethylene oxide/propylene oxide copolymers such as Pluronic F77 available from the BASF Corporation. Amounts of these materials may range from 0.1 to about 5%, preferably from about 0.3 to about 3%, optimally from about 0.5 to about 1% by weight.

Volatile and nonvolatile silicone oils may also be incorporated into compositions according to the present invention. Preferred silicones include the polydimethyl siloxanes having from 3 to about 9 silicon atoms. Examples of silicone oils useful herein include: Dow Corning 344, Dow Corning 345 and Dow Corning 200. Silicone copolyols may also be useful, a preferred material being commercially available as Amersil DMC 357. Amounts of these materials may range from about 0.1 to about 20%, preferably from about 0.2 to about 3%, optimally between about 0.4 and 1.5% by weight.

Adjunct components of compositions according to the present invention may include fragrances, colorants, sunscreens, bacteriostats and combinations thereof, each at a level sufficient to perform their function. Generally, these materials will be present in amounts anywhere from about 0.01 to about 5% by weight of the compositions.

Sticks according to the present invention will preferably be clear. By the term clear is meant either translucent or transparent. Typically, the clear sticks will allow at least 2%, preferably more than 10%, optimally more than 50% of light to be transmitted through a one inch diameter stick.

The following Examples will more fully illustrate embodiments of this invention. All parts, percentages and proportions referred to herein and in the appended claims are by weight unless otherwise indicated.

EXAMPLE 1

A set of compositions were formulated to evaluate the effect of the propoxylated $C_6$–$C_{20}$ alcohol carboxylate (Velsan D8P-3) on clarity of the resultant sticks. These compositions are outlined in the Table below.

TABLE I

| COMPONENT | A | B | C | D |
|---|---|---|---|---|
| PHASE I | | | | |
| Westchlor A2Z8106 | 51.00 | 51.00 | 51.00 | 51.00 |
| Liponic EG-7 | 3.00 | 3.00 | 3.00 | 3.00 |
| Velsan D8P-16* | 1.50 | — | — | — |
| Velsan P8-3** | — | 1.50 | — | — |
| Velsan D8P-3*** | — | — | — | 1.50 |
| Macol 57 | 0.80 | 0.80 | 0.80 | 0.80 |
| Amersil DMC357 | 0.40 | 0.40 | 0.40 | 0.40 |
| Pluronic F-77 | 0.50 | 0.50 | 0.50 | 0.50 |
| F,D & C Blue No. 1 | 0.10 | 0.10 | 0.10 | 0.10 |
| PHASE II | | | | |
| Dipropylene Glycol | 20.50 | 20.50 | 20.50 | 20.50 |
| Propylene Glycol | 18.70 | 18.70 | 18.70 | 18.70 |
| Millithix 925 | 2.50 | 2.50 | 2.50 | 2.50 |

*Cetyl PPG-2-Isodeceth-7-Carboxylate
**Isopropyl $C_{12-15}$ Pareth-9-Carboxylate
***Isopropyl PPG-2-Isodeceth-7-Carboxylate Each of the compositions were formed by first combining phase I components in the order listed. These components were mixed while maintaining heat at 65° C. Phase II was then formed by combining dipropylene glycol and propylene glycol with heating to 110° C. Millithix 925® (DBMSA) was vigorously mixed into the phase II blend which was heated to 127° C. Thereafter, phase II was mixed until clear. Phase II after cooling to 110° C., was added to phase I held at 65° C. Fragrance was then added and the resultant mixture poured into molds.

Composition A was slightly cloudy upon pouring and became cloudy/opaque after gelation. As the fragrance was added, it was observed that the fragrance did not fully solubilize and formed flecks of precipitate.

Composition B was clear when poured and became slightly cloudy after gelation. Composition C was slightly cloudy at pouring and also after gelation. As the fragrance was added, it did not fully solubilize and formed flecks of precipitate. By contrast, Composition D was clear when poured and remained clear after gelation.

Based on these results, it is seen that Composition D is superior to that of A, B and C. Composition D owes its clarity to the presence of Velsan D8P-3, i.e. Isopropyl-PPG-2-Isodeceth-7-Carboxylate.

EXAMPLE 2-8

A further series of compositions according to the present invention are reported in the table below.

TABLE II

| COMPONENT | WEIGHT % | | | | | | |
|---|---|---|---|---|---|---|---|
| | 2 | 3 | 4 | 5 | 6 | 7 | 8 |
| Westchlor A2Z8106 | 51 | 51 | 41 | 41 | 51 | 51 | 51 |
| Dypropylene Glycol | 24 | 24 | 22 | 22 | 10 | 10 | 24 |
| Propylene Glycol | 15 | 15 | 15 | 15 | 29 | 29 | 15 |
| Liponic EG-7 | 3 | 5 | 5 | 1 | 3 | 1 | 3 |
| Millithix 925 | 3 | 1 | 1 | 5 | 3 | 3 | 3 |
| Velsan D8P-3 | 0.5 | 0.5 | 2.5 | 0.5 | 0.5 | 3.5 | 1.9 |
| Fragrance | 1 | 1 | 1 | 1 | 1 | 1 | 1 |
| Macol 57 | 0.5 | 0.5 | 0.5 | 0.5 | 0.5 | 0.5 | 0.5 |
| Pluronic F77 | 1.4 | 1.4 | 1.4 | 1.4 | 1.4 | 0.4 | — |
| Amersil DMC 357 | 0.5 | 0.5 | 0.5 | 0.5 | 0.5 | 0.5 | 0.5 |
| F, D & C Blue No. 1 | 0.1 | 0.1 | 0.1 | 0.1 | 0.1 | 0.1 | 0.1 |

Although this invention has been described with reference to specific Examples, it will be apparent to one skilled in the art that various modifications will be suggested, all of which are within the spirit and purview of this invention.

What is claimed is:

1. An antiperspirant stick composition of good clarity comprising:
   (i) from about 1 to about 50% by weight of an astringent antiperspirant-active salt;
   (ii) from about 5 to about 60% by weight of a $C_2$–$C_{12}$ polyhydric alcohol;
   (iii) from about 0.5 to about 10% by weight of dibenzyl monosorbitol acetal; and
   (iv) from about 0.1 to about 10% by weight of is propyl PPG-2 isodeceth-7 carboxylate.

2. A composition according to claim 1, further comprising from about 0.1 to about 10% by weight of zinc glycinate.

3. A composition according to claim 1, wherein the polyhydric alcohol is selected from the group consisting of dipropylene glycol and propylene glycol.

4. A composition according to claim 1, wherein the carboxylate is present in an amount from 1 to 2%.

5. A composition according to claim 4, wherein the dibenzyl monosorbitol acetal is present in an amount from 1.5 to 5%.

6. A composition according to claim 1, wherein the carboxylate is present in an amount from 0.8 to 5%.

* * * * *